(12) United States Patent
Zille et al.

(10) Patent No.: US 11,737,849 B2
(45) Date of Patent: Aug. 29, 2023

(54) FACIAL RECONSTRUCTION IMPLANT KIT

(71) Applicant: OsteoMed LLC, Addison, TX (US)

(72) Inventors: Devid R. Zille, Addison, TX (US);
Johanna Scheeh, Addison, TX (US)

(73) Assignee: OsteoMed LLC, Addison, TX (US)

( * ) Notice: Subject to any disclaimer, the term of this patent is extended or adjusted under 35 U.S.C. 154(b) by 402 days.

(21) Appl. No.: 16/891,570

(22) Filed: Jun. 3, 2020

(65) Prior Publication Data
US 2020/0375686 A1 Dec. 3, 2020

Related U.S. Application Data

(60) Provisional application No. 62/856,498, filed on Jun. 3, 2019.

(51) Int. Cl.
| | |
|---|---|
| *A61B 50/30* | (2016.01) |
| *A61B 34/10* | (2016.01) |
| *B33Y 10/00* | (2015.01) |
| A61B 17/00 | (2006.01) |
| A61B 50/00 | (2016.01) |
| A61B 17/88 | (2006.01) |
| A61B 17/86 | (2006.01) |
| A61B 17/17 | (2006.01) |
| A61B 17/16 | (2006.01) |

(52) U.S. Cl.
CPC .............. *A61B 50/30* (2016.02); *A61B 34/10* (2016.02); *B33Y 10/00* (2014.12); *A61B 17/1673* (2013.01); *A61B 17/176* (2013.01); *A61B 17/86* (2013.01); *A61B 17/8875* (2013.01); *A61B 2017/00526* (2013.01); *A61B 2034/108* (2016.02); *A61B 2050/005* (2016.02); *A61B 2050/3006* (2016.02); *A61B 2050/3007* (2016.02)

(58) Field of Classification Search
CPC .... A61B 2050/3006; A61B 50/30–2050/3015; A61B 50/20–50/22
See application file for complete search history.

(56) References Cited

U.S. PATENT DOCUMENTS

| | | | |
|---|---|---|---|
| 8,267,246 B2* | 9/2012 | Bettenhausen | A61B 50/30 206/439 |
| 2007/0205123 A1* | 9/2007 | Bettenhausen | A61B 50/34 206/370 |
| 2011/0071573 A1* | 3/2011 | Sixto | A61B 50/36 606/286 |
| 2018/0206933 A1* | 7/2018 | Healey | A61B 50/22 |

* cited by examiner

*Primary Examiner* — Zade Coley
(74) *Attorney, Agent, or Firm* — K&L Gates LLP

(57) ABSTRACT

In an aspect, a method of manufacturing a surgical kit includes providing one or more medical devices based on a three-dimensional (3D) image of an anatomical structure. The method additionally includes providing packaging based on the 3D image, and providing the surgical kit utilizing the packaging and the one or more medical devices. In another aspect, a surgical kit has one or more contoured packaging surface having a contour that matches a contour of an anatomical structure. The contoured packaging surface has one or more features for receiving one or more medical devices provided based on the contour in the 3D image. The surgical kit additionally has a lid connected under pressure with the one or more contoured packaging surface. The lid has apertures for sterilization of components of the one or more medical devices situated between the lid and the contoured packaging surface.

9 Claims, 6 Drawing Sheets

FACIAL RECONSTRUCTION IMPLANT KIT

CROSS-REFERENCE TO RELATED APPLICATION

The present application claims priority to U.S. Provisional Application No. 62/856,498 filed Jun. 3, 2019 and entitled "FACIAL RECONSTRUCTION IMPLANT KIT," the disclosure of which is incorporated by reference herein in its entirety.

TECHNICAL FIELD

The present disclosure generally relates to surgical kits that may be used during osteotomy procedures, such as facial reconstruction procedures. The present disclosure also provides a method for manufacturing such surgical kits.

BACKGROUND

An osteotomy procedure is generally performed to correct bone-related defects and/or abnormalities. The procedure may include a surgical operation where a surgeon (e.g., an orthopedic surgeon) cuts a bone to shorten, lengthen, and change its alignment. For example, an illustrative osteotomy procedure, such as orthognathic surgery (also referred to as corrective jaw surgery) may include surgically cutting or dividing the bones of mandible and/or maxilla and then repositioning the cut pieces in the desired alignment to correct a deformity in the jaw. Some osteotomy procedures may involve reconstructing a cosmetic defect—which may be a birth defect, or may be caused by other factors, for instance, deformities formed due to other corrective surgical procedures—by embedding one or more implants (e.g., a titanium mesh/plate) at/around the defective region to correct the defect. To illustrate, excising a tumor from a tumorous bone generally produce cosmetic defects that can have negative effects on a patient's appearance. Therefore, to improve the patient's lifestyle, surgeons often reconstruct the defect by inserting one or more implants at/around the defective region of the bone to reconstruct the bone to its original form.

The currently used manufacturing techniques for implants allows for reconstruction of the cosmetic defects. However, the conventional production techniques are costly and can require complex intraoperative processes. Further, surgeons, in some scenarios, may be required to change the shape of an implant in the operating room during surgery. For example, in the operating room during the surgery, a surgeon may need to trim the edges of an implant (e.g., titanium mesh) to affix the implant at a desired position. Furthermore, a surgeon normally selects surgical guides and surgical screws with associated drills and drivers from among a large array of such implements, and determines the correct guides, screws, drills, and drivers by trial and error during the surgical procedure. Not only the surgical facility is also required to maintain a large inventory of surgical guides and surgical screws with associated drills and drivers, these actions (i.e., changing the shape of the implant and selecting surgical guides and screws from an array of options) are difficult and time consuming, especially when performed during the surgery, and therefore can cause complications for a patient.

SUMMARY

The present disclosure describes various embodiments of a surgical kit and method of manufacturing the surgical kit.

The disclosed surgical kit may be designed to provide visual aid to the surgeon during the surgery. To illustrate, the surgical kit may be designed to have one or more contoured surfaces that are custom designed for every patient in that each one of the one or more contoured surfaces matches contour of one or more anatomical structures recreated using a 3D image (e.g., MRI, CT scan, etc.) of the one or more defective anatomical structures. In aspects, the disclosed surgical kit may be designed to include one or more surgical devices (e.g., pre-formed implants) for use during a surgery. To further illustrate, the surgical kit may also include one or more surgical devices, such as pre-formed implants (e.g., titanium mesh), which may be positioned/disposed on the contoured surface corresponding to the structural feature that the surgeon plans to reconstruct. As such, the surgical kits manufactured with the foregoing design visually aids the surgeon during surgery in that the contoured design helps the surgeon in selecting the right implant from the one or more pre-formed implants based on the portion of the anatomical structure being reconstructed and facilitates precise reconstruction of the cosmetic defects as the implants are specifically designed based on the contour of the patient.

In some embodiments, the surgical kit may be not be fully custom designed for each patient. For example, some surgical kits may be designed based on age, ethnicity, gender, or generic physical makeup of the anatomical structure upon which the surgeon is to operate. Nonetheless, the semi-custom design of the surgical kit also visual aids the surgeon during the surgery and also helps the surgeon in selecting the right implant from the one or more pre-formed implants based on the portion of the anatomical structure being reconstructed.

In some embodiments, the surgical kit unit may also have one or more features that provides additional visual aid to the surgeon. For example, in the case of a custom designed surgical kit, the contoured surface of the kit may include one or more features, such as apertures, which may be holes for receiving surgical screws that are selected based on thickness/depth of bone exhibiting the contour in the 3D image of the desired bone of the patient. In the case of a semi-custom surgical kit, the contoured surface of the kit may have one or more features, which may be holes for receiving surgical screws that are selected based on generic thickness/depth of the bone in question. In either case, the surgical kit may additionally include surgical fixation devices (e.g., screws) that are selected ahead of time for performing the surgery, thus avoiding the need for surgeons to determine the correct lengths and/or widths of surgical screws during surgery, and also avoiding the need for the surgical facility to stock a large inventory of surgical screws.

In some embodiments, the surgical kit disclosed herein may be a part of a larger surgical kit that includes other medical devices (e.g., surgical guides, surgical drills, etc.) that may be used during the surgery. In some embodiments, instead of being a part of a larger surgical kit, the surgical kit disclosed herein includes features that allow the other medical devices (e.g., surgical guides, surgical drills, etc.) to append to the surgical kit. In some embodiments, the surgical kit disclosed herein include features that allow medical devices such as surgical guides to be disposed within the surgical kit.

In an aspect, a method of manufacturing a surgical kit includes providing one or more medical devices based on a three-dimensional (3D) image of an anatomical structure. The method additionally includes providing packaging based on the 3D image of the anatomical structure. The method further includes providing the surgical kit utilizing the packaging and the one or more medical devices. In aspects, the medical devices may include pre-formed implants that have been stamped into a shaped contour using contoured plates 3D printed (or fabricated using other additive manufacturing techniques) from a 3D image containing an image of a surface of a bone exhibiting the contour. At least part of the packaging may also be 3D printed based on this same contour. The surgical kit may have a lid connected under pressure with the one or more contoured packaging surface. The lid has apertures formed therein for sterilization of at least part of at least one of the one or more medical devices situated beneath the lid and atop the one or more contoured packaging surface.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed methods and apparatuses, reference should be made to the implementations illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

For the sake of illustration and clarity, this disclosure primarily presents examples and embodiments with respect to orthognamic/facial surgical applications. However, it should be appreciated that the disclosure is not intended to be limited to the examples and embodiments with respect to orthognamic surgical applications, but is to be accorded the widest scope consistent with the principles and novel features of the surgical kits disclosed ahead. Thus, the description ahead is provided to enable any person skilled in the art to make or use the disclosure. Various modifications to the disclosure will be readily apparent to those skilled in the art, and the generic principles of the use and manufacturing of surgical kits defined herein may be applied to other variations as well (e.g., using the invention while performing different (e.g., metacarpals-related) reconstruction surgeries.

The detailed description set forth below, in connection with the appended drawings, is intended as a description of various possible configurations and is not intended to limit the scope of the disclosure. Rather, the detailed description includes specific details for the purpose of providing a thorough understanding of the inventive subject matter. It will be apparent to those skilled in the art that these specific details are not required in every case and that, in some instances, well-known structures and components are shown in block diagram form for clarity of presentation.

Figure 1:
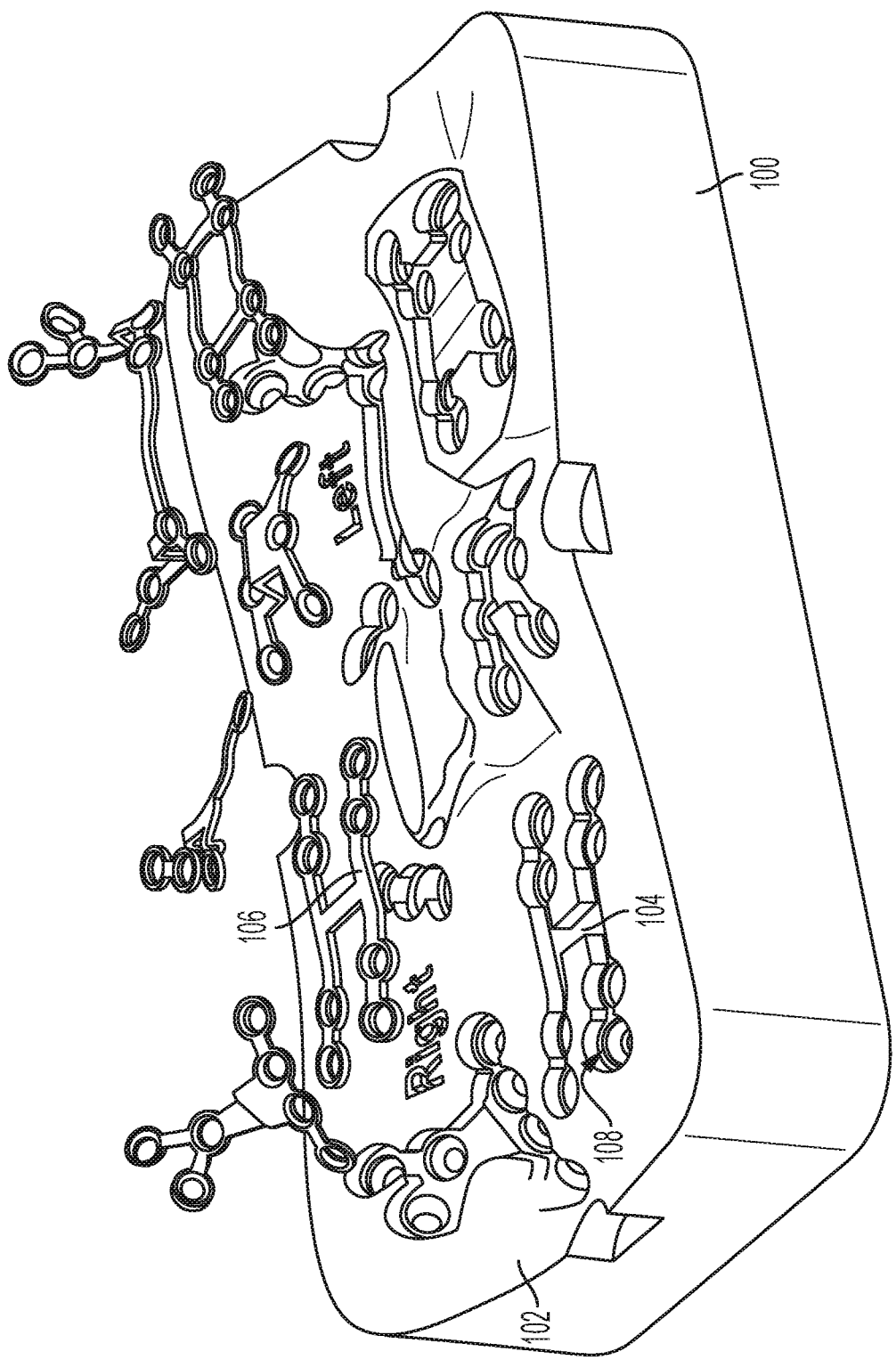
FIG. 1 is a perspective view of a contoured packaging surface in accordance with embodiments of the present disclosure.

FIG. 1 illustrates a contoured packaging surface 100 in accordance with embodiments of the present disclosure. The contoured packaging surface 100 may be a part of a surgical kit, an example of which is further described ahead in FIG. 3. The contoured packaging surface 100 may have a top surface 112, sides 114, a bottom surface 116. In aspects, the sides 112 may be parallel to each other and may include one or more features, such as features 118, for carrying the contoured packaging surface 100. In aspects, the bottom surface 116 is designed such that it can stack (or nest within) on other packaging surfaces. To illustrate, bottom surface 116 may include features (e.g., lining at the bottom boundary of the bottom surface 116) that facilitates stacking the packaging surface 100 together with another packing surface so as to prevent them from coming apart. In aspects, the features at the bottom surface 116 may be such that the packaging surface 100 and the other packing surface it could be attached to can be drawn away from each other with the application of some finite force. In aspects, the other packaging surface upon which the packaging surface 100 may be stacked on may include features, such as recesses, for receiving medical devices that are selected and/or manufactured based on the contour and/or selected surgical screws.

In aspects, the top surface 112 may have a contour 102 that matches contour of an anatomical structure (e.g., nasal bone) recreated using a 3D image (e.g., MRI, CT scan, etc.) of the defective anatomical structure upon which a surgeon may operate. In other words, the contour 102 may resemble the recreated contours of the defective anatomical structure, which the surgeon may reconstruct. In aspects, the contour 102 may include multiple contours (e.g., contours of different sides of the anatomical structure) of the defective anatomical structure. To illustrate, assume that a surgeon plans to reconstruct a nasal bone defect in a patient; the contour 102, in such a scenario, may include multiple contours, where each contour of the multiple contours may match the contour of the portion of the nasal bone which is to be reconstructed by the surgeon. For example, the part of the top surface 112 labeled "Left" may include a contour that match the left side of the nasal defect which is to be reconstructed and the one labeled "Right" may include a contour that match the right side of the nasal defect which is to be reconstructed.

In aspects, the contour 102 may match contours multiple different anatomical structures (e.g., nasal bone, jaw bone, etc.) recreated using 3D images (e.g., MRI, CT scan, etc.) of the defective anatomical structures In other words, the contour 102 may resemble the recreated contours of multiple defective anatomical structures. In aspects, the contour 102 may include multiple contours for each one of the defective anatomical structures. To illustrate, assume that a surgeon plans to reconstruct both a nasal bone and a jaw bone defect in a patient; the contour 102, in such a scenario, may include one or more contours for each one of the defect. In such embodiments, the part of the top surface 112 depicted to be labeled "Left" may be labeled "Nasal bone" indicating that the contours in that portion of the top surface are recreated contours of the nasal bone, and the part of the top surface 112 depicted to be labeled "Right" may be labeled "Jaw bone" indicating that the contours in that portion of the top surface are recreated contours of the jaw bone.

In aspects, the contour 102 may further be designed to include one or more surgical devices (e.g., pre-formed implants, surgical guides, etc.) for use during surgery. To illustrate, the contoured packaging surface 100 may have one or more features, such as recesses 104, for receiving implants, such as contoured bone plates 106, which may be pre-formed using different material such as trimmed titanium mesh as described in U.S. patent application Ser. No. 16/378,446, which is incorporated in this application in its entirety). In aspects, the one or more surgical devices may be positioned on the contour 102 at a shape that substantially matches a shape of the anatomical structure where the one or more surgical device may be used. Continuing the above-noted example of nasal bone defect, the contoured bone plates 106 positioned on the "Left" side may be used by the surgeon to reconstruct the left side of the patient's nasal bone, and the contoured bone plates 106 positioned on the "Right" side may be used to reconstruct the right side of the patient's nasal anatomical structure. Similarly, continuing the above-noted example of both nasal and jaw bone defect, the contoured bone plates 106 positioned on the "Nasal bone" side may be used by the surgeon to reconstruct the nasal bone, and the contoured bone plates 106 positioned on the "Jaw bone" side may be used to reconstruct the jaw bone.

In aspects, the contour 102 may be custom designed for every patient in that contour 102 match contour of one or more three-dimensional (3D) images of one or more anatomical structures, such as one or more facial bones of a patient in a magnetic resonance image (MRI), computerized tomography (CT) scan, or the like. To illustrate, a custom designed contour 102 may include contours of different portions of one or more anatomical structures for every patient that will be operated upon by the surgeon. In such contours, the one or more pre-formed implants (e.g., titanium mesh) positioned/disposed on the contoured surface may be precisely designed and manufactured for every patient, thereby reducing the possibility of the surgeon having to change the shape of the implant during surgery, as is the case with conventional implants. In some embodiments, however, the surgical kit may be not be fully custom designed for each patient. For example, some surgical kits may be designed based on age, ethnicity, gender, or generic physical makeup of the anatomical structure upon which the surgeon is to operate.

In some embodiments, the contoured packaging surface 100 may also include one or more features that provide additional aid to the surgeon. For example, in the case of a custom designed surgical kit, the contour 102 may include one or more features, such as apertures 108, which may be holes for receiving surgical screws that are selected based on thickness/depth of bone exhibiting the contour in the 3D image of the desired bone of the patient. On the other hand, in the case of a semi-custom surgical kit, the contoured surface of the kit may have one or more features, which may be holes for receiving surgical screws that are selected based on generic thickness/depth of the bone in question. In either case, the surgical kit may additionally include surgical fixation devices (e.g., screws) that are selected ahead of time for performing the surgery, thus avoiding the need for surgeons to determine the correct lengths and/or widths of surgical screws during surgery, and also avoiding the need for the surgical facility to stock a large inventory of surgical screws.

Figure 2:
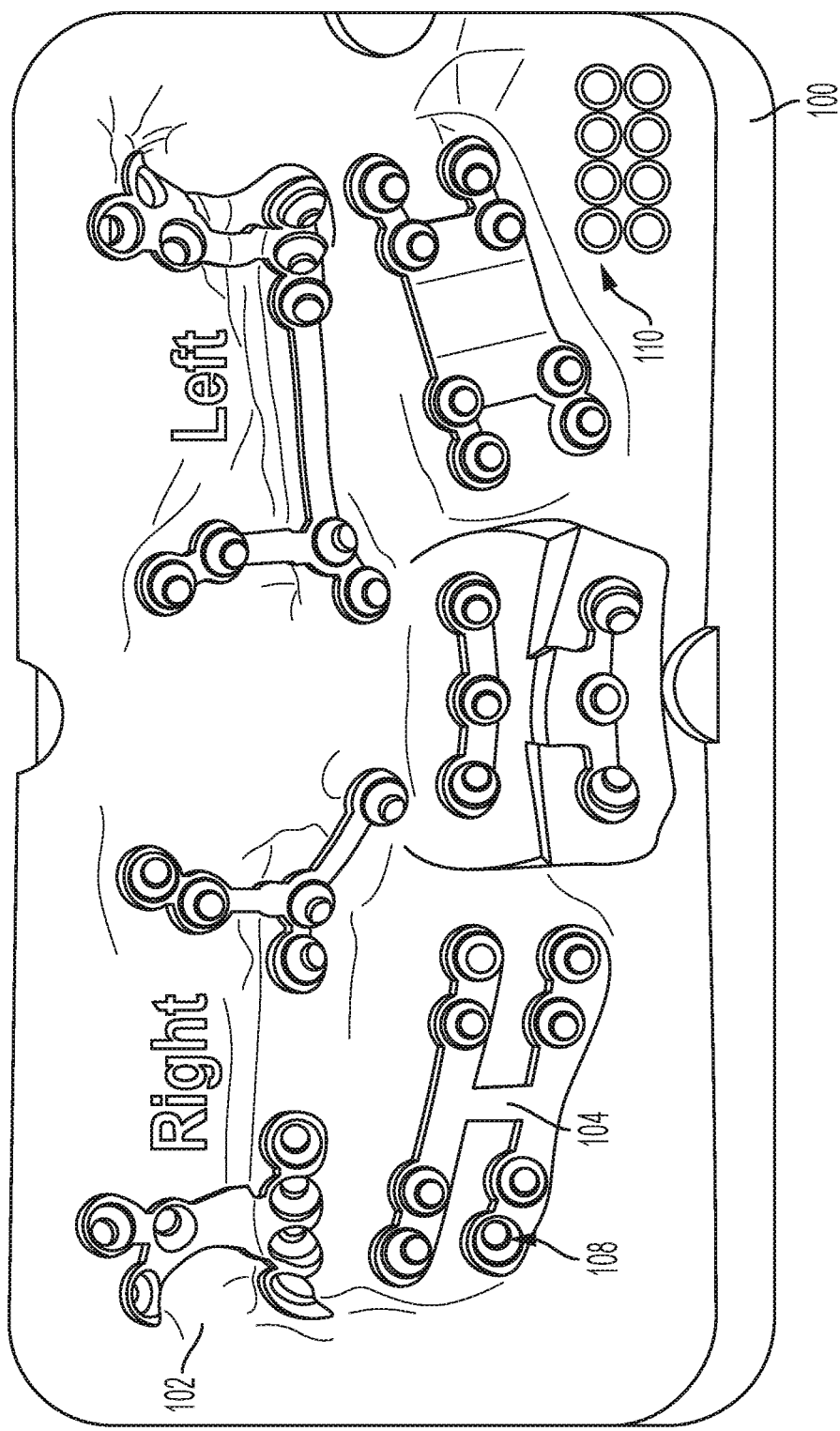
FIG. 2 is a top view of the contoured packaging surface of FIG. 1.

FIG. 2 provides a top view of the contoured packaging surface 100 of FIG. 1. As shown in FIG. 2, in addition to contour 102, recesses 104 for bone plates 106, and apertures 108, the contoured packaging surface 100 may have additional apertures 110. The additional apertures may be through holes that receive surgical screws, which may be extra screws or may permit some or all of the apertures 108 to be open for sterilization purposes (as is further described below). In aspects, the contoured packaging surface 100 may include extra implants as duplicates.

Figure 3:
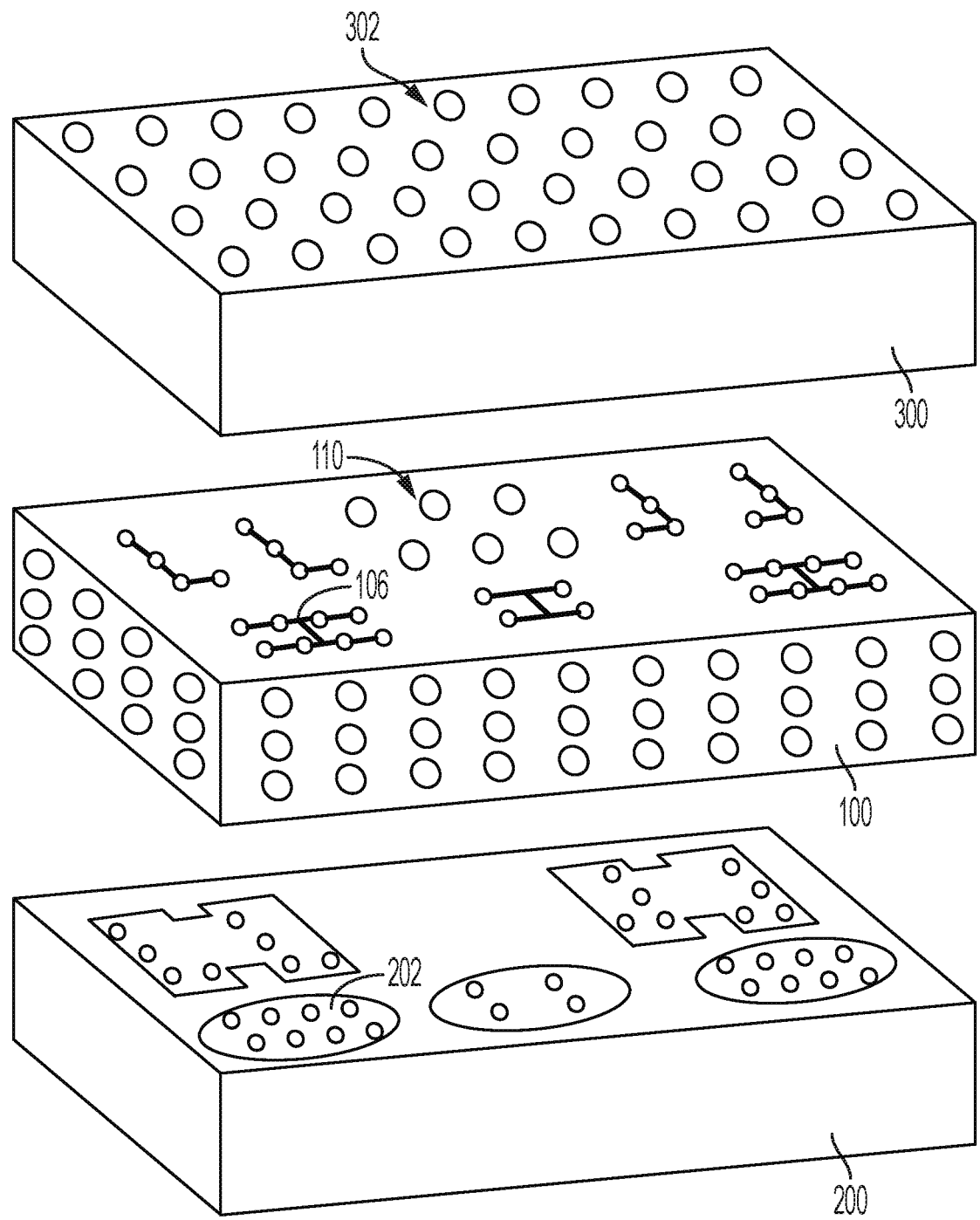
FIG. 3 is a perspective view of a surgical kit having layered packaging surfaces and a lid in accordance with embodiments of the present disclosure.

FIG. 3 illustrates a surgical kit having contoured packaging surface 100 and layered packaging surface 200, and a lid 300. Here, contoured packaging surface 100 corresponds to the contoured packaging surface of FIGS. 1 and 2; it is depicted to be opened on a bottom so that it can be stacked or nested atop contoured packaging surface 200. In the illustrated example, the layered packaging surface 200 may have features, such as recesses, for receiving medical devices (e.g., surgical guides 202 and/or drills and drivers) that are selected and/or manufactured based on the contour and/or selected surgical screws. In aspects, layered packaging surface 200 may be contoured or flat; if contoured, the layered packaging surface 200 may exhibit a same contour as surface 100. Layered packaging surface 200 may be connected under pressure beneath contoured packaging surface 100. In this case, additional apertures 110 on a top and/or sides of layered packaging surface 100 may allow sterilization of medical device components (e.g., screw threads, surgical guides 202, and/or drills and screw drivers) situated between the surfaces 100 and 200. In this way, a layered package of custom manufactured and selected medical devices (e.g., bone plates, surgical screws, surgical guides, drills, and/or screw drivers) for a specific surgery on a specific patient may be provided in such a way that it can be inserted in an autoclave and successfully sterilize all of the medical devices prior to surgery. Alternatively or additionally, the medical devices and the interior kit surfaces may all be sterilized and sealed prior to shipping and delivery of the completed kit to a surgical facility at which the surgery is performed.

As mentioned above, packaging surface 100 has a contour that matches a contour of an anatomical structure (e.g., nasal bone), and the contoured packaging surface 100 has one or more features (e.g., recesses) formed therein for receiving one or more medical devices (e.g., bone plates and surgical screws) provided based at least in part on the contour of the anatomical structure in a 3D image (e.g., MRI, CT scan, etc.). The lid 300 may be connected under pressure with the contoured packaging surface 100, and the lid 300 may have apertures 302 formed therein for sterilization of at least part of at least one of the one or more medical devices (e.g., bone plates and screw heads) situated beneath the lid 300 and atop the contoured packaging surface 100. In aspects, the lid 300 may have a reverse contour that mates with the contour of the contoured packaging surface 100 in such a way that the medical devices (e.g., bone plates and surgical screws) are secured in place when the lid 300 is connected to the contoured packaging surface 100.

Figure 4:
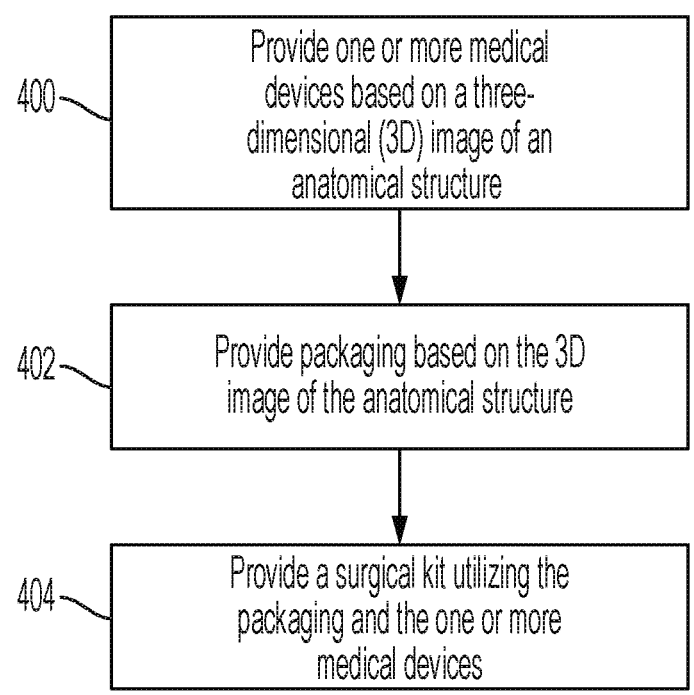
FIG. 4 is a flow diagram illustrating a method of manufacturing a surgical kit in accordance with embodiments of the present disclosure.

FIG. 4 illustrates a method of manufacturing a surgical kit in accordance with embodiments of the present disclosure. Beginning at block 400, the method includes providing one or more medical devices based on a three-dimensional (3D) image of one or more anatomical structure. For example, block 400 may include using a 3D printer to manufacture contoured implants that match a contour of the anatomical structure of the 3D image. In aspects, the 3D printer may be used to print contoured plates that exhibit the contour of the portion of the anatomical structure being reconstructed. In aspects, the contoured plates be stamped into a shape matching the contour. The shaped contoured plates may then be trimmed to provide the contoured implants. Alternatively or additionally, block 400 may include at least one of selecting or manufacturing one or more surgical guides based on the contour of the 3D image. Alternatively or additionally, the block 400 may include selecting one or more surgical screws based on a thickness of bone exhibiting the contour of the 3D image. Alternatively or additionally, block 400 may include selecting at least one of one or more drills or one or more screwdrivers based on the selection of the one or more surgical screws. The method may proceed from block 400 to block 402.

At block 402, the method includes providing packaging based on the 3D image of the anatomical structure. For example, block 402 may include using a 3D printer to manufacture at least one contoured packaging surface exhibiting a contour of the anatomical structure of the 3D image. Alternatively or additionally, block 402 may include using the 3D printer to manufacture at least two packaging surfaces that are configured to be at least one of nested or stacked one atop another, at least one of the at least two packaging surface being the contoured packaging surface. Alternatively or additionally, block 402 may include providing recesses for receiving contoured implants, the recesses having through holes for receiving screws selected based on a thickness of bone exhibiting the contour of the 3D image. The method may proceed from block 402 to block 404.

At block 404, the method includes providing the surgical kit utilizing the packaging and the one or more medical devices. For example, block 404 may include situating the one or more medical devices in the packaging, and connecting the packing under pressure with a lid having apertures formed therein for sterilization of the one or more medical devices. It is also envisioned that block 404 may include sterilizing (e.g., in an autoclave) the interior of the surgical kit and sealing the surgical kit (e.g., in a medical grade plastic wrap or shrink wrap). The sealed kit may further be irradiated before shipping, with instructions to the surgical facility to sterilize the kit again prior to surgery.

Figure 5:
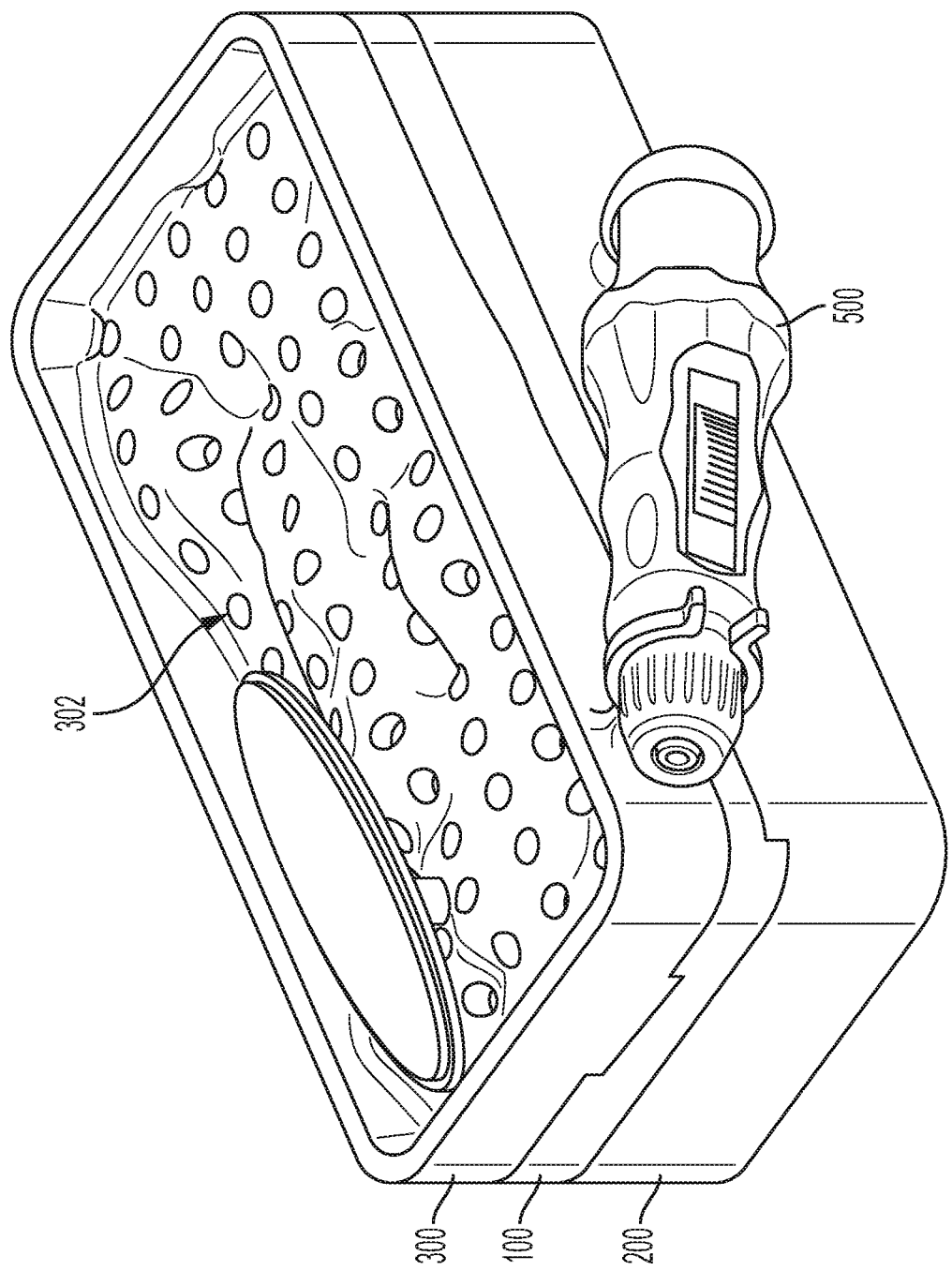
FIG. 5 is a perspective view of a surgical kit including the contoured packaging surface of FIG. 1, the layered packaging surface lid of FIG. 3.

FIG. 5 illustrates a surgical kit manufactured according to the method of FIG. 4 and including the contoured packaging surface 100, the layered packaging surface 200, and the lid 300 of FIG. 3. Here, the layered packaging surface 200 is configured as a bottom of the kit. Apertures 302 in lid 300 permit sterilization of medical device components located between contoured packaging surface 100 and lid 300. Features provided on sides of the lid 300 and layered packaging surface 200 are configured to receive and hold a screwdriver handle 500.

Figure 6:
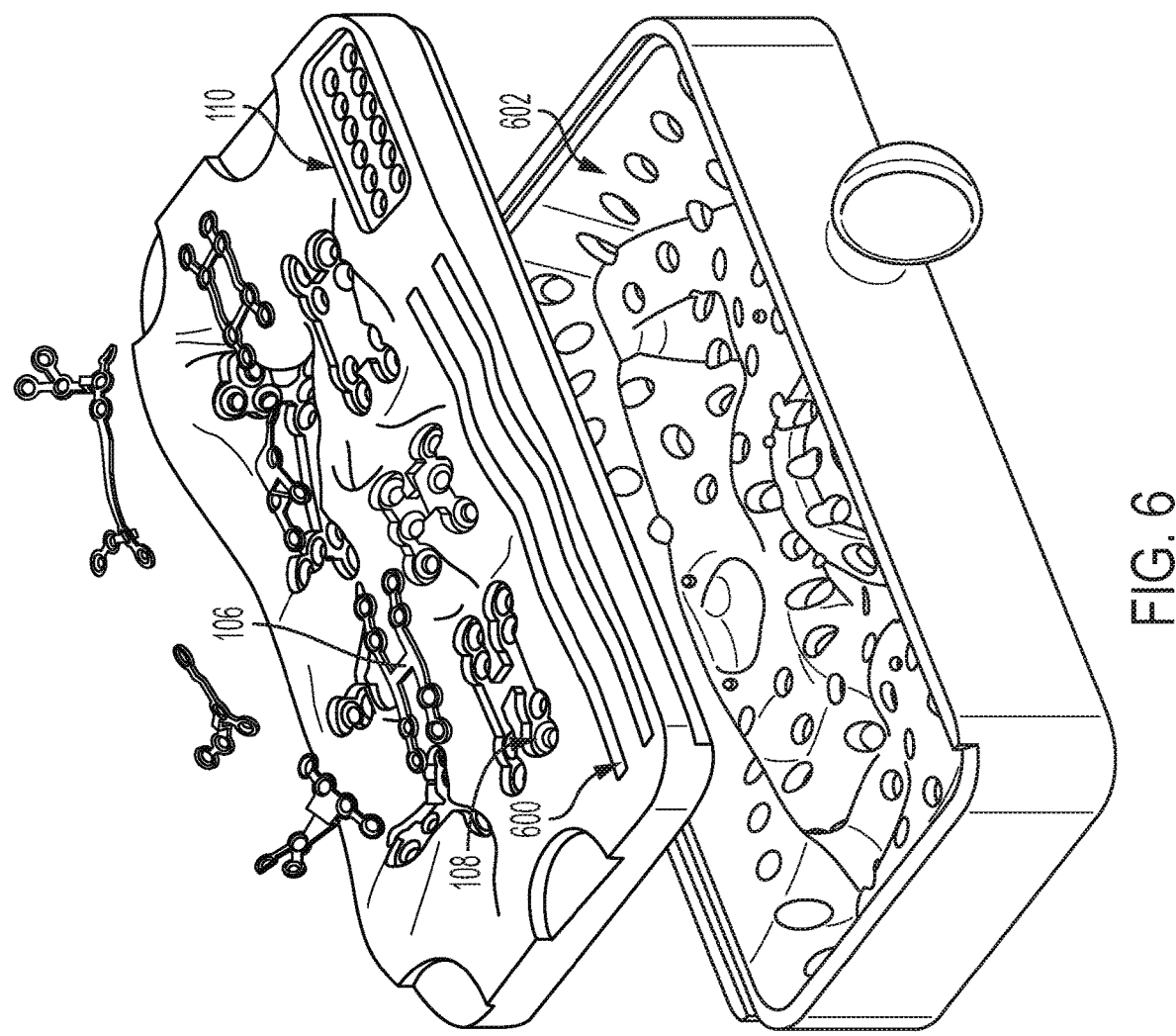
FIG. 6 is a exploded view of the contoured packaging surface of FIG. 1 and the layered packaging surface of FIG. 5.

FIG. 6 illustrates additional features of the contoured packaging surface 100 and the layered packaging surface 200 of the kit of FIG. 5. For example, the layered packaging surface 200, being configured as a bottom of the kit, has apertures formed therein that permit sterilization of medical device components located between layered packaging surface 200 and contoured packaging surface 100. For example, the layered packaging surface 200 provides a contoured space 602 with features for receiving surgical guides for the bone plates 106. Also, contoured packaging surface 100 has features 600, such as recesses, that are configured to receive surgical drills and driver shafts that are suitable for use with the screws stored in apertures 108 and/or 110. With apertures formed in a bottom of the surgical kit, as shown, need is reduced or eliminated for apertures in a side of the kit or additional apertures in the contoured packaging surface 100. Stated differently, all of the apertures in the contoured packaging surface 100 may located in an interior region of the kit, and all of the apertures may be used to hold the selected surgical screws.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Skilled artisans will also readily recognize that the order or combination of components, methods, or interactions that are described herein are merely examples and that the components, methods, or interactions of the various aspects of the present disclosure may be combined or performed in ways other than those illustrated and described herein.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C) or any of these in any combination thereof.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

Although embodiments of the present application and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

The invention claimed is:

1. A surgical kit, comprising:
   at least one contoured packaging surface having a contour that is configured to match a contour of an anatomical structure, wherein at least a portion of the contour of the at least one contoured packaging surface is curved, the contoured packaging surface having one or more features formed therein for receiving one or more medical devices provided based at least in part on the contour of the anatomical structure in a three-dimensional (3D) image;
   a lid connected under pressure with the at least one contoured packaging surface and having apertures formed therein for sterilization of at least part of at least one of the one or more medical devices situated beneath the lid and atop the at least one contoured packaging surface; and
   a layered packaging surface having one or more features formed therein for receiving one or more medical devices, wherein the contoured packaging surface is configured to be nested or stacked atop the layered packaging surface.

2. The surgical kit of claim 1, wherein the one or more medical devices include contoured implants manufactured to match the contour of the anatomical structure of the 3D image.

3. The surgical kit of claim 1, wherein the features include recesses configured to receive at least one of one or more contoured implants, one or more surgical guides, one or more drills, or one or more screwdrivers.

4. The surgical kit of claim 1, wherein the contoured packaging surface has apertures for sterilization of at least part of at least one of the one or more medical devices that is situated beneath the contoured packaging surface.

5. The surgical kit of claim 1, wherein the one or more medical devices include one or more surgical guides at least one of selected or manufactured based on the contour of the anatomical structure of the 3D image.

6. The surgical kit of claim 1, wherein the one or more medical devices include one or more surgical screws selected based on a thickness of bone exhibiting the contour of the anatomical structure of the 3D image.

7. The surgical kit of claim 6, wherein the one or more medical devices include at least one of one or more drills or one or more screwdrivers selected based on the selection of the one or more surgical screws.

8. The surgical kit of claim 1, wherein the features include one or more through holes configured to receive one or more surgical screws selected based on a thickness of bone exhibiting the contour of the anatomical structure of the 3D image.

9. The surgical kit of claim 1, wherein the contour of the anatomical structure that matches the contour of the contoured packaging surface comprises a contour of a defective anatomical structure.

* * * * *